(12) United States Patent
Yonezawa

(10) Patent No.: US 6,801,651 B2
(45) Date of Patent: Oct. 5, 2004

(54) VISUAL INSPECTION APPARATUS

(75) Inventor: Eiji Yonezawa, Aichi (JP)

(73) Assignee: Nidek Co., Ltd., Aichi (JP)

( * ) Notice: Subject to any disclaimer, the term of this patent is extended or adjusted under 35 U.S.C. 154(b) by 513 days.

(21) Appl. No.: 09/726,122

(22) Filed: Nov. 30, 2000

(65) Prior Publication Data

US 2001/0012393 A1 Aug. 9, 2001

(30) Foreign Application Priority Data

Nov. 30, 1999 (JP) ........................................ P. 11-340241

(51) Int. Cl.⁷ ............................................... G06K 9/00
(52) U.S. Cl. ....................................... 382/145; 382/144
(58) Field of Search .............................. 382/141–151; 356/237.1, 237.2, 237.4, 237.5, 394; 348/86, 87, 125, 126

(56) References Cited

U.S. PATENT DOCUMENTS

| 4,995,702 | A | | 2/1991 | Aruga ..................... 350/331 R |
|---|---|---|---|---|
| 5,686,958 | A | | 11/1997 | Shibasaki et al. .............. 348/70 |
| 5,726,443 | A | | 3/1998 | Immega et al. ........... 250/227.2 |
| 5,923,430 | A | * | 7/1999 | Worster et al. .............. 356/394 |
| 6,222,624 | B1 | * | 4/2001 | Yonezawa ................. 356/237.1 |
| 6,556,291 | B2 | * | 4/2003 | Yonezawa ................. 356/237.2 |

FOREIGN PATENT DOCUMENTS

| EP | 0 930 498 A2 | 7/1999 | .......... G01N/21/88 |
| JP | 11-83455 | 3/1999 | .......... G01B/11/24 |
| WO | 95/20811 | 8/1995 | ............ G09G/3/22 |

OTHER PUBLICATIONS

Japanese Abstract No. 06167460, dated Jun. 14, 1994.
Japanese Abstract No. 60113937, dated Jun. 20, 1985.
Japanese Abstract No. 04099346, dated Mar. 31, 1992.
Japanese Abstract No. 09292207, dated Nov. 11, 1997.
Japanese Abstract No. 62044609, Feb. 26, 1987.

* cited by examiner

Primary Examiner—Vikkram Bali
(74) Attorney, Agent, or Firm—Sughrue Mion, PLLC

(57) ABSTRACT

In a visual inspection apparatus for visual inspection of an object, a plurality of monochrome images obtained from an object are used to prepare a plurality of computed color images. The computed color images are switchingly displayed on a color display for visual inspection.

21 Claims, 3 Drawing Sheets

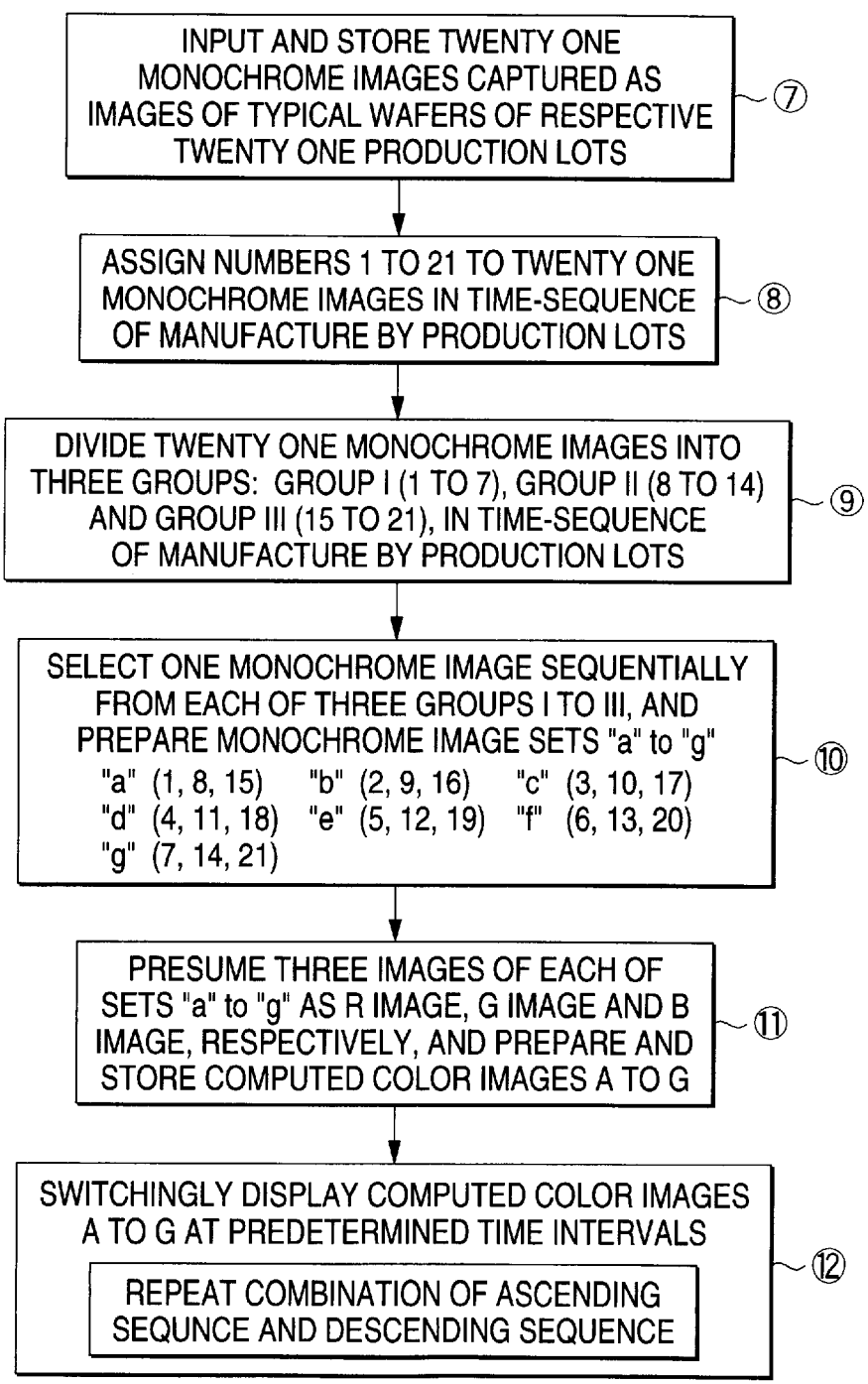

VISUAL INSPECTION APPARATUS

BACKGROUND OF THE INVENTION

The present invention relates to a visual inspection apparatus for inspecting variations in the thickness of an object to be inspected, such as a semiconductor wafer, inconsistencies which have occurred during the working of minute patterns, or variations between production lots.

Macroscopic inspection as to the presence or absence of variations in the thickness of a semiconductor wafer, inconsistencies which have occurred during the working of a minute pattern, and variations between production lots of the semiconductor wafers has been generally performed such that a semiconductor wafer is observed under a dark field by obliquely radiating intensive light onto the semiconductor wafer or that a semiconductor wafer is observed with regular reflection using a large-scale plane illumination. In this inspection, an operator observes variations in colors while inclining the semiconductor wafer in various directions to detect inconsistencies which have occurred during the working of the semiconductor wafer. To detect variations between production lots of the semiconductor wafers, the operator must depend on his own memory.

Direct visual inspection of a wafer to be performed by an operator poses difficulty in maintaining cleanliness or involves occurrence of contamination because an operator need to approach the wafer. Thus, direct visual inspection presents an obstacle in improving quality of a wafer. Further, inspection of a wafer which requires an operator to incline a wafer in various directions imposes a load on an operator. For these reasons, automatic inspection of a wafer has been desired.

A conceivable method for automating inspection of a wafer is to observe images captured by a CCD camera or the like using a mechanism for inclining a wafer in the same manner as does an operator. Such a mechanism involves a complicated construction. In a case where the images of a wafer are captured while the wafer is inclined greatly, the resultant images become distorted or defocused.

In the case of checking variations in respective production lots of wafers on the basis of an operator's memory, the inconsistencies is difficult to be recognized.

The present invention has been conceived in light of the drawbacks of the background art and is aimed at providing a visual inspection apparatus capable of readily and correctly inspecting inconsistencies which have arisen during the working of an object to be processed or variations between respective production lots of the objects.

SUMMARY OF THE INVENTION

The present invention provides the followings:

(1) A visual inspection apparatus for visual inspection of an object, the apparatus comprising:
image input means for inputting a plurality of monochrome images obtained from at least one object;
image preparing means for preparing a plurality of computed color images based on the monochrome images thus inputted;
a color display; and
display control means for switchingly displaying the computed color images on the color display.

(2) The apparatus of (1), wherein the display control means switchingly displays the computed color images at predetermined time intervals.

(3) The apparatus of (1), wherein the display control mans swtichingly displays the computed color images in a predetermined order.

(4) The apparatus of (1), further comprising:
illumination means for illuminating the object with an illumination light;
wavelength selection means for selecting a narrow band light having a desired center wavelength from the illumination light or a reflected light from the object illuminated with the illumination light, the wavelength selection means capable of variably setting the desired center wavelength;
capturing means for capturing an image of the object using the narrow band light thus selected;
wherein the image input means inputs the monochrome images captured by the capturing means using the narrow band lights having different center wavelengths.

(5) The apparatus of (4), wherein the wavelength selection means variably sets the desired center wavelength to be an arbitrary value falling within 450 nm to 800 nm.

(6) The apparatus of (1), wherein the image preparing means divides the inputted monochrome images into sets each having three monochrome images, and presumes the three monochrome images of each set as red, green and blue images, respectively, to prepare an associated one of the computed color images.

(7) The apparatus of (6), wherein:
the image input means inputs the monochrome images obtained using lights of different wavelengths; and
the image preparing means divides the monochrome images into the sets based on the wavelengths.

(8) The apparatus of (7), wherein:
the image input means inputs the monochrome images obtained using different narrow band lights having respective center wavelengths falling within a range of 450 nm to 800 nm; and
the image preparing means divides the monochrome images into the sets based on the centered wavelengths of the lights used to obtain the monochrome images.

(9) The apparatus of (8), wherein the display control means switchingly displays the computed color images on the display in an order determined based on the centered wavelengths of the lights used to obtain the monochrome images, the order being at least one of an order from a shorter wavelength to a longer wavelength and an order from a longer wavelength to a shorter wavelength.

(10) The apparatus of (6), wherein:
the image input means inputs the monochrome images obtained from the plural objects manufactured by different production lots; and
the image preparing means divides the monochrome images into the sets based on time-sequence of the manufacture by the production lots.

(11) The apparatus of (10), wherein the display control means switchingly displays the computed color images on the display in an order determined based on the time-sequence of the manufacture by the production lots, the order being at least one of an order from an earlier manufacture to a later manufacture and an order from a later manufacture to an earlier manufacture.

(12) The apparatus of (6), wherein the image input means inputs, as the monochrome image, at least four monochrome images.

(13) A visual inspection apparatus for visual inspection of an object, the apparatus comprising:
an image processor which stores a processing program and prepares a plurality of computed color images based on a plurality of inputted monochrome images in accordance with the processing program;
a color display; and a display controller which stores a displaying program and controls the display to switchingly display the computed color images in accordance with the displaying program.

(14) The apparatus of (13), further comprising an image pick-up element which obtains a monochrome image of the object and inputs the obtained monochrome image to the image processor.

(15) The apparatus of (14), further comprising an illumination unit which illuminates the object with an illumination light.

(16) The apparatus of (13), wherein the processing program includes:

first step of dividing the inputted monochrome images into sets each having three monochrome images; and second step of presuming the three monochrome images of each set as red, green and blue images, respectively.

(17) The apparatus of (13), wherein the processing program includes:

first step of dividing the inputted monochrome images into sets each having three monochrome images based on each of wavelengths which are used for obtaining the inputted monochrome images; and second step of presuming the three monochrome images of each set as red, green and blue images, respectively.

(18) The apparatus of (17), wherein the displaying program includes the step of displaying the computed color images in an order determined based on the wavelength.

(19) The apparatus of (13), wherein the processing program includes:

first step of dividing the inputted monochrome images into sets each having three monochrome images based on each of production lots of plural objects which are used for obtaining the inputted monochrome images; and second step of presuming the three monochrome images of each set as red, green and blue images, respectively.

(20) The apparatus of (19), wherein the displaying program includes the step of displaying the computed color images in an order determined based on the production lots.

(21) The apparatus of (13), wherein the displaying program includes the step of displaying the computed color images at predetermined time intervals and in a predetermined order.

(22) The apparatus of (13), wherein the image processor prepares at least two computed color images based on at least four inputted monochrome images.

The present disclosure relates to the subject matter contained in Japanese patent application No. Hei. 11-340241 (filed on Nov. 30, 1999), which is expressly incorporated herein by reference in its entirety.

BRIEF DESCRIPTION OF THE DRAWINGS

FIG. 3 is a flowchart for inspection of variations of wafers caused depending on production lots.

DESCRIPTION OF THE PREFERRED EMBODIMENT

Figure 1:
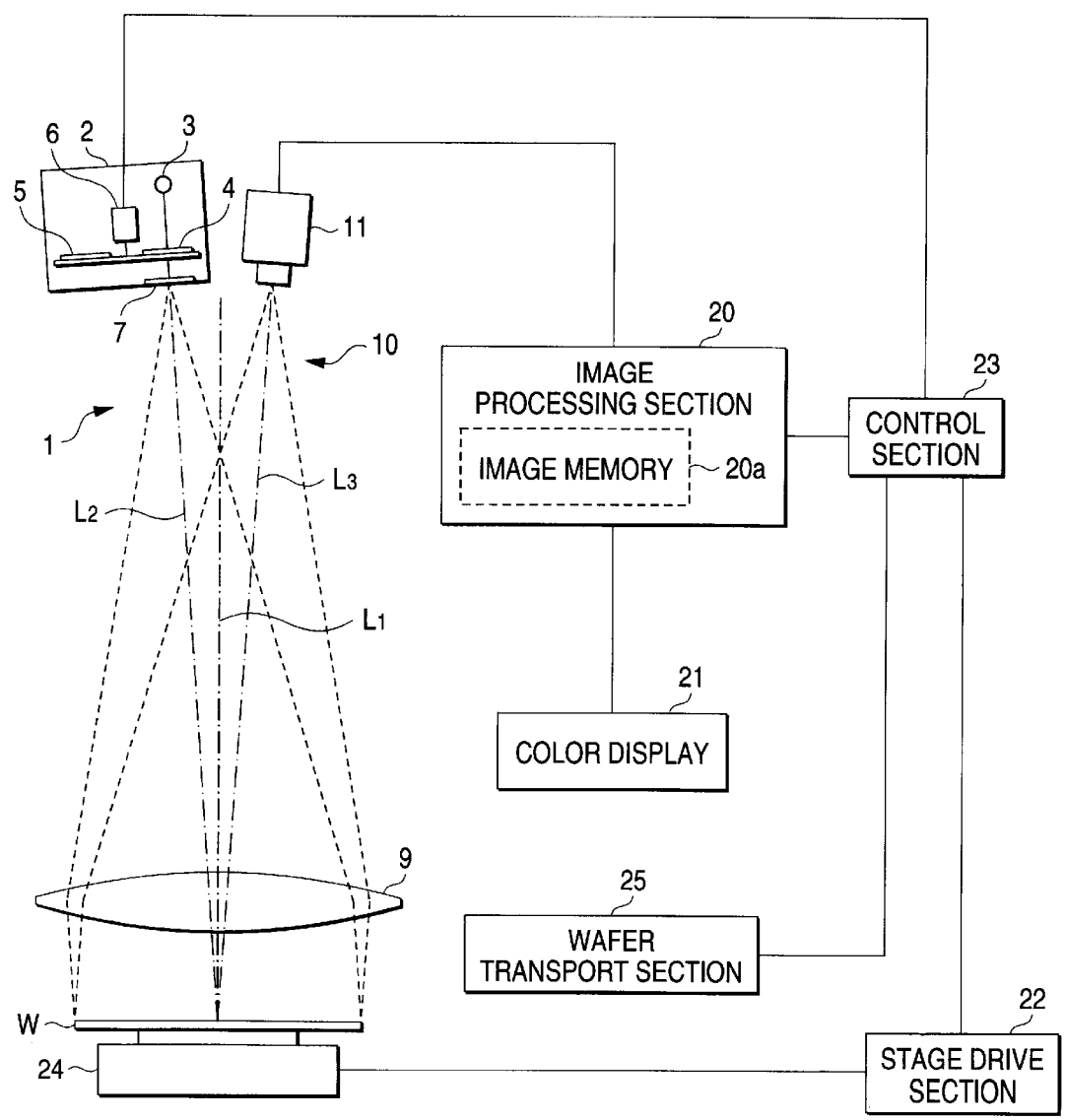
FIG. 1 is a schematic diagram showing an arrangment of an inspection apparatus according to the present invention.

A preferred embodiment of the present invention will be described hereinbelow by reference to the accompanying drawings. FIG. 1 is a diagram showing an arrangement of a visual inspection apparatus according to the present invention.

Reference numeral 1 designates an illumination optical system for illuminating a wafer W which is placed on an XY stage 24 and is to be inspected (i.e., an object). The illumination optical system 1 is equipped with an illumination unit 2 and a collimator lens 9, which is greater in diameter than an inspection surface of the wafer W. Reference numeral 10 designates an image pick-up optical system for capturing an image of the wafer W illuminated by the illumination optical system 1. The collimator lens 9 is shared between the illumination optical system 1 and the image pick-up optical system 10, and the image pick-up optical system 10 is equipped with a CCD camera 11.

The optical axis L3 of the image pick-up optical system 10 is arranged symmetrical to the optical axis L2 of the illumination optical system 1 with respect to the optical axis L1 of the collimator lens 9. As a result, the CCD camera 11 can obtain an image of an inspection surface of the wafer W with regular reflection from the wafer W illuminated by the illumination optical system 1. The camera 11 is arranged so as to obtain an image of the wafer W in a direction substantially perpendicular to a surface of the wafer W while avoiding interference with the illumination unit 2. In the present embodiment, each of the angle formed between the optical axes L1 and L2 and the angle formed between the optical axes L1 and L3 is set to be three degrees. Since the inclination of the optical axis L3 relative to the inspection surface of the wafer W is not great, an image is less susceptible to distortion or defocusing.

The optical axis L2 of the illumination optical system 1 may be arranged to be identical to the optical axis L1 of the lens 9 to illuminate the wafer W at a right angle, and the optical axis L3 of the image pick-up optical system 10 may be arranged to be identical to the optical axis L2 of the illumination optical system 1. In this case, using of a half mirror, the image pick-up optical system 10 obtains an image of the inspection surface of the wafer W with the regular reflection from the inspection surface while avoiding interference between the illumination unit 2 and the camera 11.

The illumination unit 2 comprises a halogen lamp 3 serving as a light source; a rotary plate 5 having a plurality of wavelength selection filters 4 and an opening for white illumination; a motor 6 for rotating the rotary plate 5; and a diffusion plate 7. The filters 4 selectively convert white illumination light emitted from the lamp 3 into narrow-band lights having respective center wavelengths. The plurality of filters 4 are provided so as to switch over the center wavelengths of narrow-band lights at predetermined intervals. In the present embodiment, to obtain twenty one images of different wavelengths, the filters are so designed as to convert white illumination light selectively into narrow-band lights of twenty one types, the center wavelengths of which are distributed at predetermined intervals and fall within a range of 450 nm to 800 nm.

The rotary plate 5 is rotated by the motor 6, and a desired filter 4 or an opening is selectively disposed on an optical path. The light that has passed through the filter 4 or the opening is diffused by the diffusion plate 7, thereby producing diffused illumination light having sufficiently uniform brightness. The thus-diffused light is substantially collimated by the lens 9 to the parallel illumination light, which illuminates the wafer W placed on the stage 24.

The regular reflection from the wafer W illuminated by illumination light is converged by the lens 9, so that an image of substantially the entire surface of the wafer W is formed on the camera 11 having the image pick-up element.

The rotary plate 5 having the filters 4, etc. may be provided in the image pick-up optical system 10 side (i.e., in front of the camera 11). Further, the wavelength of white illumination light may be changed using a monochromator in stead of the wavelength selection filters 4.

Image data output from the camera 11 are input to an image processing section 20. The image processing section 20 subjects the image data that have been subjected to predetermined processing, such as analog-to-digital conversion, to required pre-processing such as noise removal and correction of sensitivity of the camera 11. The image processing section 20 then prepares a computed color image from the input image S (described in detail later). Reference numeral 20a designates an image memory which stores the image output from the camera 11 (or the image that has been subjected to pre-processing) and the prepared computed color image therein. Reference numeral 21 designates an image display section (i.e., a color display or a color monitor) where the prepared computed color images are displayed as an animation under control of the image processing section 20 (described in detail later). Reference numeral 22 designates a stage drive section for moving the stage 24, and reference numeral 25 designates a wafer transport section for automatically moving a wafer W to the stage 24. Reference numeral 23 designates a control section for controlling the entire visual inspection apparatus.

Figure 2:
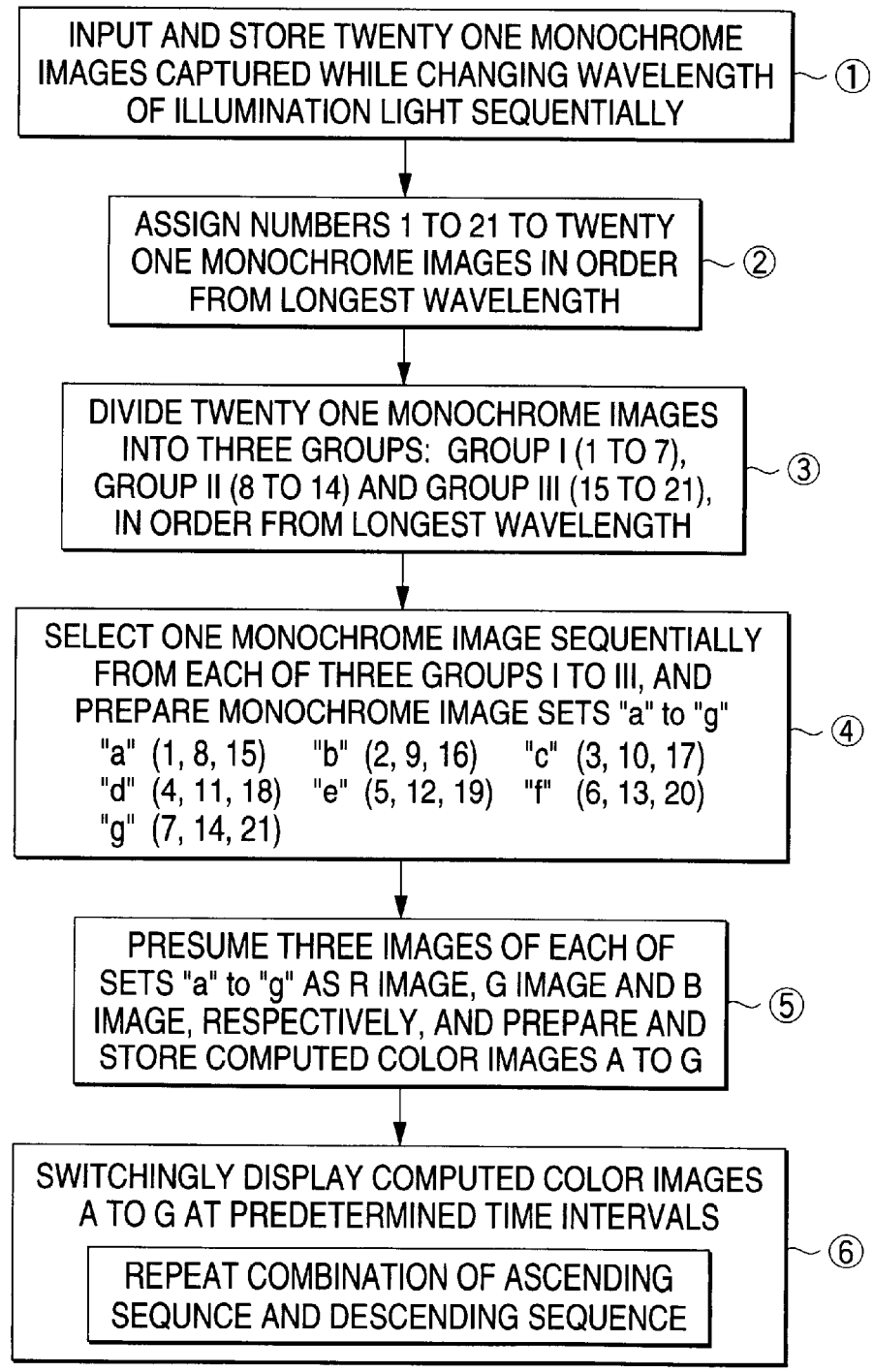
FIG. 2 is a flowchart for inspection of a single wafer W.

Next, the description will be given of a case where the visual inspection apparatus of the above-described construction is used to inspect the thickness of a resist film formed on the wafer W or inconsistencies which have arisen during the working of a minute pattern (see FIG. 2).

The control section 23 drives the motor 6 to rotate the rotary plate 5, thereby sequentially arranging the filters 4 of twenty one types on the optical path. Accordingly, the wafer W placed on the stage 24 is illuminated while the wavelengths of narrow-band lights are changed. In synchronism with the change in wavelength of illumination light caused under control of the control section 23, the image processing section 20 sequentially fetches (obtains) twenty one image data sets of the wafer W captured by the camera 11, and the thus fetched twenty one image data sets are stored in the memory 20a (1). Here, raw image data captured by the camera 11 may be fetched and stored, but as mentioned previously, image data are preferably subjected to pre-processing, such as correction of sensitivity of the camera 11 or removal of noise, before the image data are fetched and stored.

Under the illumination by narrow band light, the variations in thickness of a resist film and the working inconsistencies of a minute pattern appear as variations of the interference fringes and present different brightness change from other region on the image. Further, by sequentially changing the wavelengths of narrow band lights, the change in color appears similarly to the case where the wafer W is inclined, which color change can be obtained as the change in brightness on the images. However, since the images, which have been obtained while the wavelengths of lights are changed, are monochrome images having shades of gray, even when the obtained images are observed in their present forms, the change in the monochrome images greatly differ from the chromatic change in images recognized by an operator's eye. Simple shades of gray make it difficult for the operator to visually recognize a difference.

In the present invention, in order to enable the operator to observe shades of gray as the chromatic change, the image processing section 20 prepares computed color images from three monochrome images. The thus-prepared color images are displayed on the display 21 as an animation. A method of preparing the computed color images and a method of displaying the computed color images will now be described.

Numbers of 1 to 21 are respectively assigned to twenty one monochrome images (or twenty one images which have been subjected to pre-processing) in the order from the longest wavelength (center wavelength) of the used illumination light (the narrow band light) (2). The twenty one monochrome images are divided into three groups in the order from the longest wavelength; namely, group I (numbers 1 to 7), group II (numbers 8 to 14), and group III (15 to 21) (3). One monochrome image is sequentially selected from each of the three groups I to III to prepare a monochrome image set. The monochrome image sets "a" to "g" are prepared, each set comprising three monochrome images (4).

Accordingly, there are prepared seven sets; i.e., set "a" (1, 8, 15); set "b" (2, 9, 16); set "c" (3, 10, 17); set "d" (4, 11, 18); set "e" (5, 12, 19); set "f" (6, 13, 20); and set "g" (7, 14, 21) (where numerals inside the parentheses denote the sequence of the twenty one images, i.e. the numbers assigned to the twenty one images).

The image processing section 20 presumes three images included in each of the sets "a" to "g" as a R (Red) image, a G (Green) image, and a B (Blue) image, respectively to prepare one computed color image. For instance, in set "a," image 1 is presumed as a R image; image 8 is presumed as a G image; and image 15 is presumed as a B image. In this way, images belonging to group I (i.e., 1 to 7) are presumed as R images; images belonging to group II (i.e., 8 to 14) are presumed as G images; and images belonging to group III (i.e., 15 to 21) are presumed as B images. A single computed color image is prepared from three images of one set, and in this embodiment seven computed color images A, B, C, D, E, F and G are prepared. The thus-prepared computed color images are stored in the memory 20a (5).

The images A to G stored in the memory 20 are switchingly and sequentially displayed on the display 21 as an animation. The images are displayed sequentially in a reciprocative manner. More specifically, images are displayed in the ascending sequence from image A, image B, image C, . . . , and image G and then in descending sequence from image G, image F, image E . . . , and image A. Once again, images are displayed in ascending sequence from image A, image B, image C, . . . , and image G. Display of images is repeated in this manner (6). The image processing section 20 performs a control operation such that images are automatically switched at a time interval of about 0.1 to 0.5 seconds. As a result, the operator can observe seven images A to G as an animation without involvement of effort.

In terms of the sense of visual capability, a human experiences difficulty in perceiving abrupt and discontinuous changes in display of images. For this reason, after images A through G have been displayed in ascending sequence, the images are displayed in descending sequence. Display of images in both ascending and descending sequences is repeated. Continuous and reciprocative display of images enables observation of a wafer closely analogous to that which has hitherto been performed by inclination of a wafer W.

If sharp changes arise in the images A to G, three monochrome images may be prepared while interpolating variation in brightness of the images in each of sets "a" to "g", in order to prepare additional computed color images to be inserted between the images A to G. This increases the number of images to be combined to form an animation, and thus realizes smooth display of images. The time interval at which one image is switched over to another image may be smoothly varied to enable observation of a change in a more natural manner, thereby facilitating visual observation of the wafer W.

As mentioned above, three monochrome images of a single wafer W which have been captured under different requirements are presumed as an R image, a G image, and a B image. A computed color image is prepared from these three images, and the thus-prepared computed color image is displayed. As compared with observation of the wafer W using monochrome images, observation of the wafer W using the computed color image enables the operator to readily perceive, as a difference in color, inconsistencies in the thickness of a resist film or inconsistencies that have occurred during the working of a minute pattern. For example, inconsistencies are emphasized as a reddish image or a bluish image visually.

A plurality of computed color images which have been prepared under gradually varying conditions are sequentially displayed on the display 21. An animation (colored animation) closely analogous to that which has hitherto been observed by the human eye while the wafer W is inclined can be observed without involvement of inclination of the wafer W.

The description has been given of a case that a single wafer W is observed using the computed color images prepared while changing the wavelengths of illumination lights. The present invention is not limited to observation of a single wafer, but may be applied to observation of plural wafers of the same type. For example, typical images (monochrome images) of twenty one respective production lots are processed in the same manner as that mentioned previously, thereby preparing computed color images. The thus-prepared computed color images are displayed, thereby enabling observation of inconsistencies in the wafers W among the production lots, each wafer having the same pattern formed thereon. Observation of such inconsistencies will now be described (see FIG. 3).

Images of different wafers W are captured under the same conditions. Typical wafers W of respective production lots are sampled, and each of the thus-sampled wafers are placed on the stage 24 in a predetermined state for image capture one by one. Light which has been subjected to wavelength selection may be employed as illumination light for illuminating the wafer W. In order to obtain standard brightness, the opening of the rotary plate 5 is located in the optical path, whereby the wafer is illuminated by white illumination light emitted from the lamp 3. The control section 23 controls transport of the wafers W by the transport section 25 and movement of the stage 24 by the stage drive section 22 such that all the wafers W placed on the stage 24 are captured under the same conditions. Images of the wafers W captured by the camera 11 are input to the image processing section 20. The image processing section 20 stores the images into the memory 20a (7).

After respective monochrome images of the typical wafers W of the twenty one production lots have been obtained, the images are arranged in time-sequence of production lots, and numbered 1 to 21 (8). As mentioned previously, the images are divided into three groups in time-sequence of production lots; that is, group I (1 to 7), group II (8 to 14), and group III (15 to 21) (9). One monochrome image is selected sequentially from each of the groups I to III. The thus-selected three images are grouped into a single set. As a result, there are prepared seven sets "a" to "g" (10). Three images of each set are presumed as a R image, a G image, and a B image, thereby preparing a computed color image. Thus, there are prepared computed color images A to G. The thus prepared seven computed color images A to G are stored in the memory 20a (11).

The thus-stored images A to G are displayed on the display 21 in both ascending and descending sequences. Display of the images A through G in both ascending and descending sequences is repeated as an animation (12). As a result of animating display of typical images of production lots, inconsistencies among production lots appear as chromatic changes. Thus, the operator can readily perceive inconsistencies by intuition. For instance, in a case where images of production lots become gradually brighter or darker, the entire image which is prepared from computed color images and is displayed becomes reddish or bluish visually. In the event of inconsistencies arising among production lots, the color or brightness of the displayed images changes abruptly, thereby enabling the operator to readily perceive inconsistencies. Further, a portion of the displayed images having inconsistencies can be readily distinguished from the remaining portions of the displayed images through a difference in color or brightness.

In the previous embodiment, twenty one images of a single wafer or twenty one images of different wafers of the same type are captured. However, this is merely an example, and the number of images to be captured is not limited to twenty one. Two or more different computed color images can be prepared using at least four monochrome images, and the thus-prepared computed color images can be displayed switchingly on the display 21 for observation. In the case of four monochrome images, images can be grouped into several sets such as a first set (1, 2, 3) and a second set (2, 3, 4). Alternatively, four or more monochrome images may be prepared by interpolating the brightness difference between two monochrome images. Further, how to form groups and how to form sets are not limited to those mentioned previously. For instance, twenty one images may be divided into an arbitrary number of sets other than seven.

As has been described, in a case where images of a single object to be inspected are captured under varying conditions, an operator can observe an image analogous to that which has hitherto been observed with the human eye while the object is inclined. As a result, the operator can perform visual inspection of the object without involvement of direct approach to the object.

In a case where images of plural objects of the same type, which have been manufactured by different production lots, are captured, variations among production lots can be observed as an intuitively understandable image.

What is claimed is:

1. A visual inspection apparatus for macroscopic inspection of an object having at least one of a film structure and a minute pattern, the apparatus comprising:

image input means including an image pick-up optical system for picking up an image of the object in a direction substantially perpendicular to the object, the image input means inputting at least four monochrome images obtained subsequently by the image pick-up optical system using at least four kinds of narrow-band lights each having a different center wavelength;

a color display; and pseudo image preparing means for dividing the input monochrome images into at least two groups, each group including three monochrome images, and for assigning image information of the three images of each group to each color image information of red, green and blue of the color display to obtain at least two pseudo color images; and display control means for switchingly displaying the obtained pseudo color images on the color display.

2. The apparatus of claim 1, wherein the display control means switchingly displays the pseudo color images at predetermined time intervals.

3. The apparatus of claim 1, wherein the display control means switchingly displays the pseudo color images in a predetermined order.

4. The apparatus of claim 1, further comprising:

illumination means for illuminating the object with the an illumination light;

wavelength selection means for selecting a narrow band light having a desired center wavelength from the illumination light or a reflected light from the object illuminated with the illumination light, the wavelength selection means capable of variably setting the desired center wavelength;

capturing means for capturing an image of the object using the narrow band light thus selected;

wherein the image input means inputs the monochrome images captured by the capturing means using the narrow band lights each having different center wavelengths.

5. The apparatus of claim 4, wherein the wavelength selection means variably sets the desired center wavelength to be an arbitrary value falling within 450 nm to 800 nm.

6. The apparatus of claim 1, wherein the display control means switchingly displays the pseudo color images on the display in an order determined based on the centered wavelengths of the lights used to obtain the monochrome images, the order being at least one of an order from a shorter wavelength to a longer wavelength and an order from a longer wavelength to a shorter wavelength.

7. The apparatus of claim 1, wherein:

the image input means inputs the monochrome images obtained from the plural objects manufactured by different production lots; and the pseudo image preparing means divides the monochrome images into the sets groups based on time-sequence of the manufacture by the production lots.

8. The apparatus of claim 7, wherein the display control means switchingly displays the pseudo color images on the display in an order determined based on the time-sequence of the manufacture by the production lots, the order being at least one of an order from an earlier manufacture to a later manufacture and an order from a later manufacture to an earlier manufacture.

9. The apparatus of claim 1, wherein the pseudo image preparing means divides the input monochrome images into short-wavelength group, long-wavelength group and middle-wavelength group, selects one from each group in order according to wavelength to provide the group including three monochrome images, and assigns the image information of the short-wavelength group to the blue, the image information of the middle-wavelength group to the red and the image information of the long-wavelength group to the green.

10. The apparatus of claim 9, wherein the display control means switchingly displays the pseudo color images in order of wavelength and repeatedly display it in ascending and descending sequences.

11. The apparatus of claim 1, further comprising illumination means for inserting one of wavelength selection filters to an optical path and for illuminating the object with illumination lights of narrow-band selected by the wavelength selection filter.

12. The apparatus of claim 11, wherein the wavelength selection means filter variably sets the desired center wavelength of the illumination light to be an arbitrary value falling within 450 nm to 800 nm.

13. A visual inspection apparatus for macroscopic inspection of an object having at least one of a film structure and a minute pattern, the apparatus comprising:

a color display;

an image processor which stores a processing program and obtains at least two pseudo color images by inputting at least four monochrome images obtained using at least four kinds of narrow-band lights each having a different center wavelength, dividing the inputted monochrome images into at least two groups, each group including three monochrome images, and assigning image information of the three images of each group to each color image information of red, green and blue of the color display in accordance with the processing program; and a display controller which stores a displaying program and controls the display to switchingly display the obtained pseudo color images in accordance with the displaying program.

14. The apparatus of claim 13, further comprising an image pick-up element which obtains a monochrome image of the object and inputs the obtained monochrome image to the image processor.

15. The apparatus of claim 14, further comprising an illumination unit which illuminates the object with an illumination light.

16. The apparatus of claim 13, wherein the displaying program includes the step of displaying the pseudo color images in an order determined based on the centered wavelengths of the lights used to obtain the monochrome images.

17. The apparatus of claim 13, wherein the displaying program includes the step of displaying the pseudo color images at predetermined time intervals and in a predetermined order.

18. A visual inspection apparatus for macroscopic inspection of an object having at least one of a film structure and a minute pattern, the apparatus comprising:

an imaging device, including an image pick-up optical system that picks up an image of the object, the imaging device inputting at least four monochrome images obtained subsequently by the image pick-up optical system using at least four kinds of narrow-band lights each having a different center wavelength; and a pseudo image computation device that divides the inputted monochrome images into at least two groups, each group including three monochrome images, and for assigning image information of the three images of each group to each color image information of red, green and blue of the color display to obtain at least two pseudo color images.

19. The apparatus of claim 18, further comprising a color display and display controller that automatically switchingly displays the pseudo color images on the color display as an animation.

20. The apparatus of claim 18, wherein the display controller switchingly displays the pseudo color images at predetermined time intervals.

21. The apparatus of claim 18, wherein the display controller switchingly displays the pseudo color images in a predetermined order.

* * * * *